(12) United States Patent
Ortiz et al.

(10) Patent No.: US 7,691,113 B2
(45) Date of Patent: Apr. 6, 2010

(54) SCREW TIP CONTROL FOR ANASTOMOTIC RING APPLIER

(75) Inventors: Mark S. Ortiz, Milford, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 611 days.

(21) Appl. No.: 11/122,383

(22) Filed: May 5, 2005

(65) Prior Publication Data
US 2006/0253141 A1 Nov. 9, 2006

(51) Int. Cl.
*A61B 17/10* (2006.01)
*A61B 17/08* (2006.01)

(52) U.S. Cl. .................... 606/139; 606/153
(58) Field of Classification Search ......... 606/139–141, 606/151, 153, 213; 623/1.11, 1.12; 227/175.1
See application file for complete search history.

(56) References Cited

U.S. PATENT DOCUMENTS

| | | | |
|---|---|---|---|
| 5,376,098 A * | 12/1994 | Fontayne et al. ........... 606/153 |
| 5,855,312 A | 1/1999 | Toledano | |
| 6,068,636 A * | 5/2000 | Chen ........................ 606/153 |
| 6,171,321 B1 | 1/2001 | Gifford et al. | |
| 6,451,029 B1 | 9/2002 | Yeatman | |
| 6,485,496 B1 * | 11/2002 | Suyker et al. ............... 606/153 |
| 6,575,973 B1 * | 6/2003 | Shekalim ..................... 606/62 |
| 2003/0032967 A1 | 2/2003 | Park et al. | |
| 2005/0070934 A1 * | 3/2005 | Tanaka et al. .............. 606/153 |

FOREIGN PATENT DOCUMENTS

| | | |
|---|---|---|
| EP | 1520526 | 4/2005 |
| EP | 1520527 | 4/2005 |
| EP | 1520528 | 4/2005 |
| EP | 1520531 | 4/2005 |
| ES | 2218861 | 11/2004 |
| WO | WO 9917662 A1 * | 4/1999 |

OTHER PUBLICATIONS

EPO Search Report, dated Aug. 21, 2006 for EP 06252366.7-2318.
Office Action dated Jan. 4, 2006, for U.S. Appl. No. 10/675,497, filed Sep. 30, 2003.

* cited by examiner

*Primary Examiner*—(Jackie) Tan-Uyen T. Ho
*Assistant Examiner*—Dianne Dornbusch
(74) *Attorney, Agent, or Firm*—Dean Gamer

(57) ABSTRACT

A surgical instrument for applying an anastomotic ring device comprises a handle connected to an anastomotic ring deployment mechanism by a shaft. The shaft has at least one torsion member that is capable of communicating a torsional actuating force from the handle to the ring deployment mechanism. The ring deployment mechanism is configured to actuate in response to torsional actuating force communicated from the torsion member. A threaded shaft or rod may be positioned in the ring deployment mechanism to effect actuation of the ring deployment mechanism in response to torsion.

17 Claims, 17 Drawing Sheets

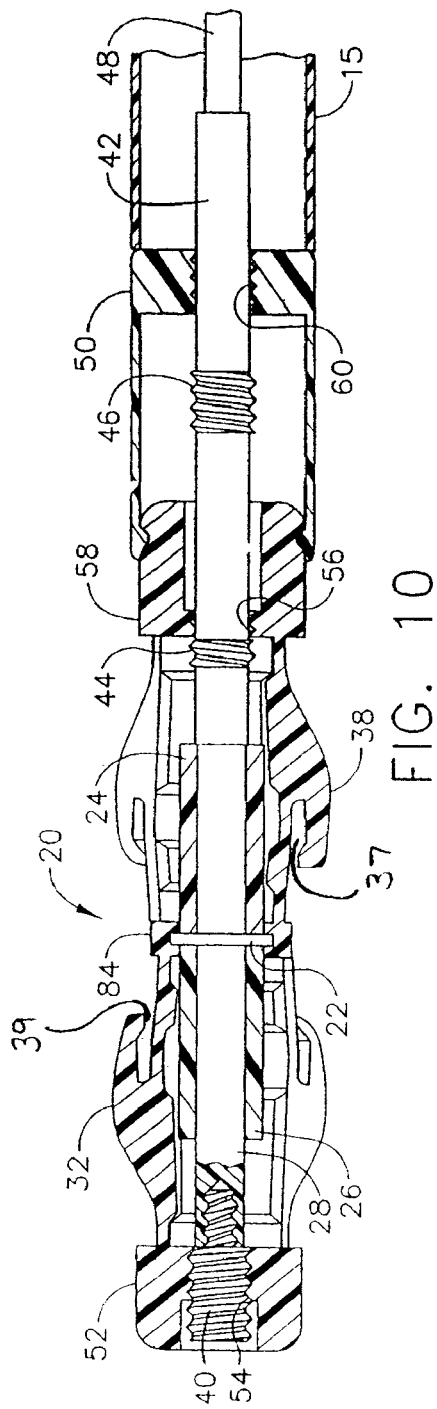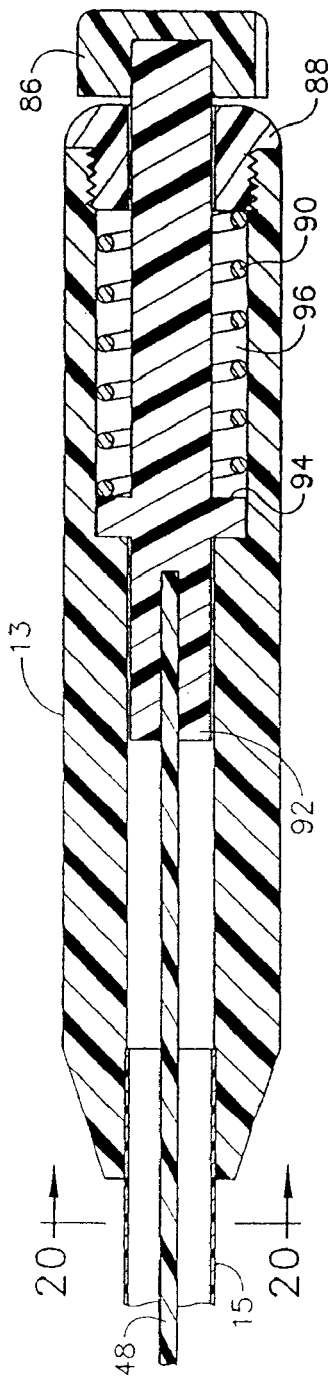

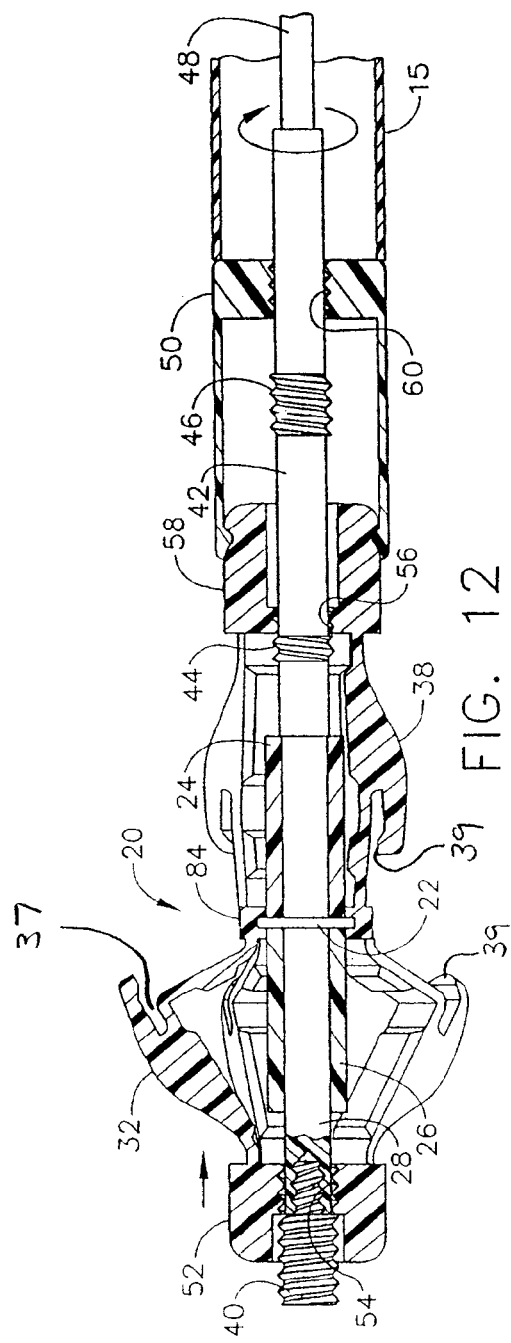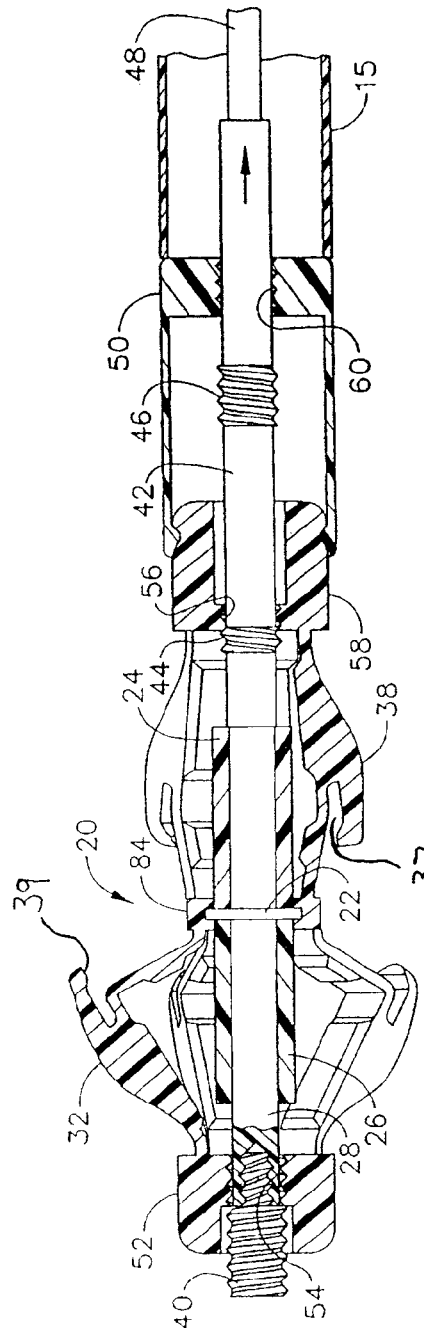

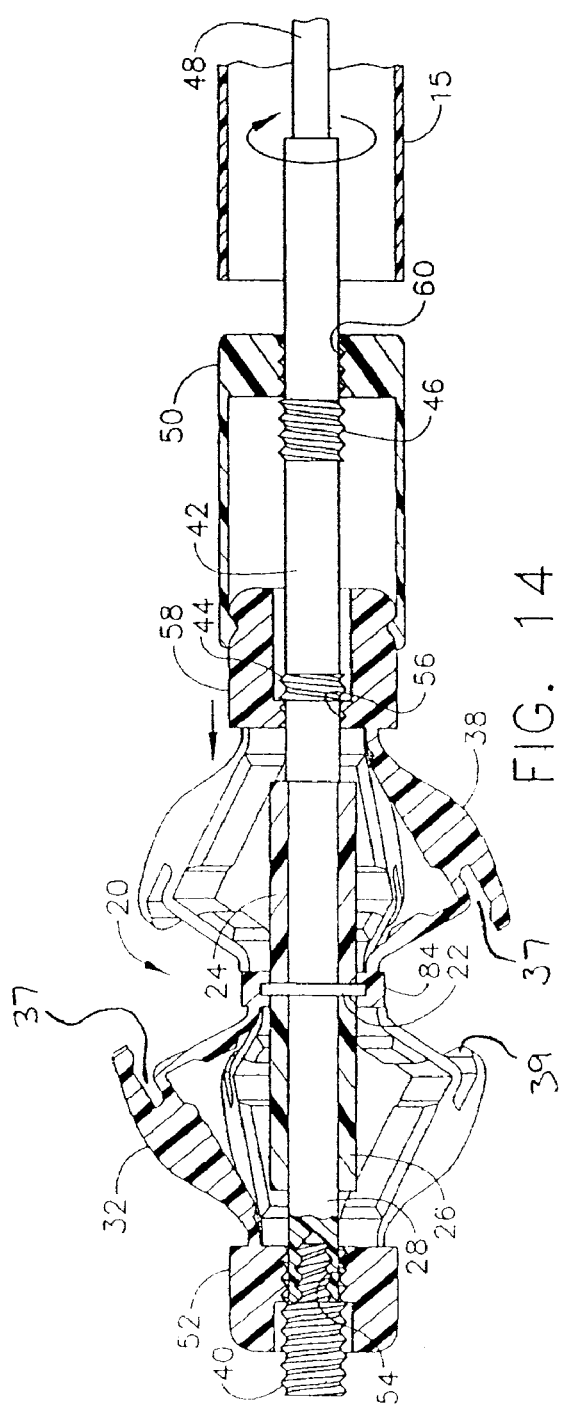
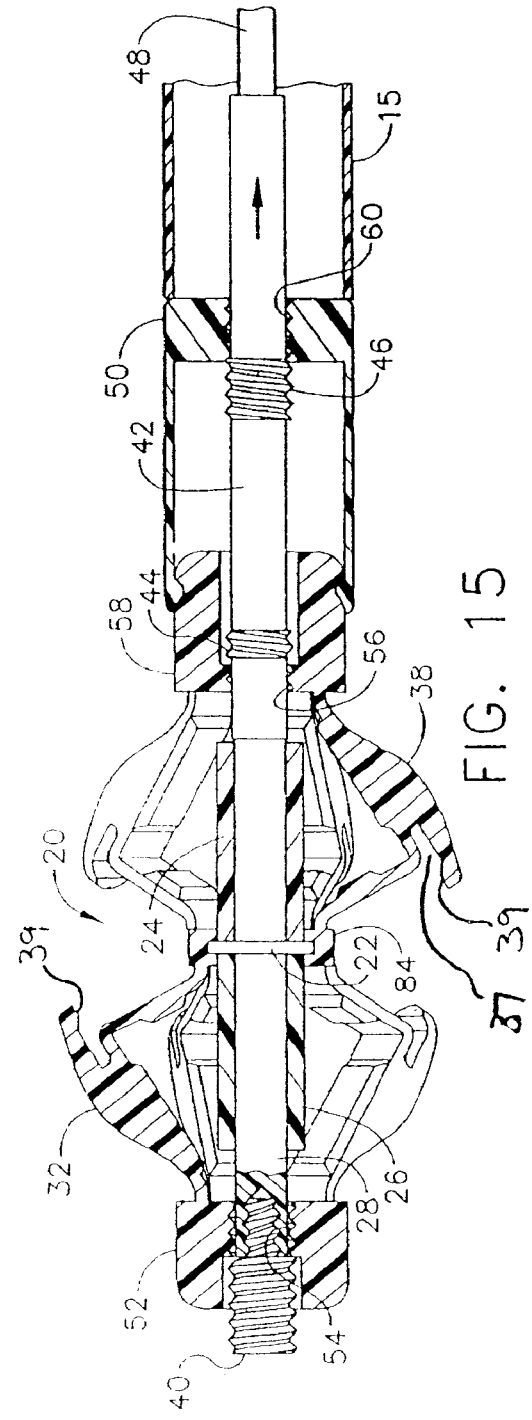
FIG. 14
FIG. 15

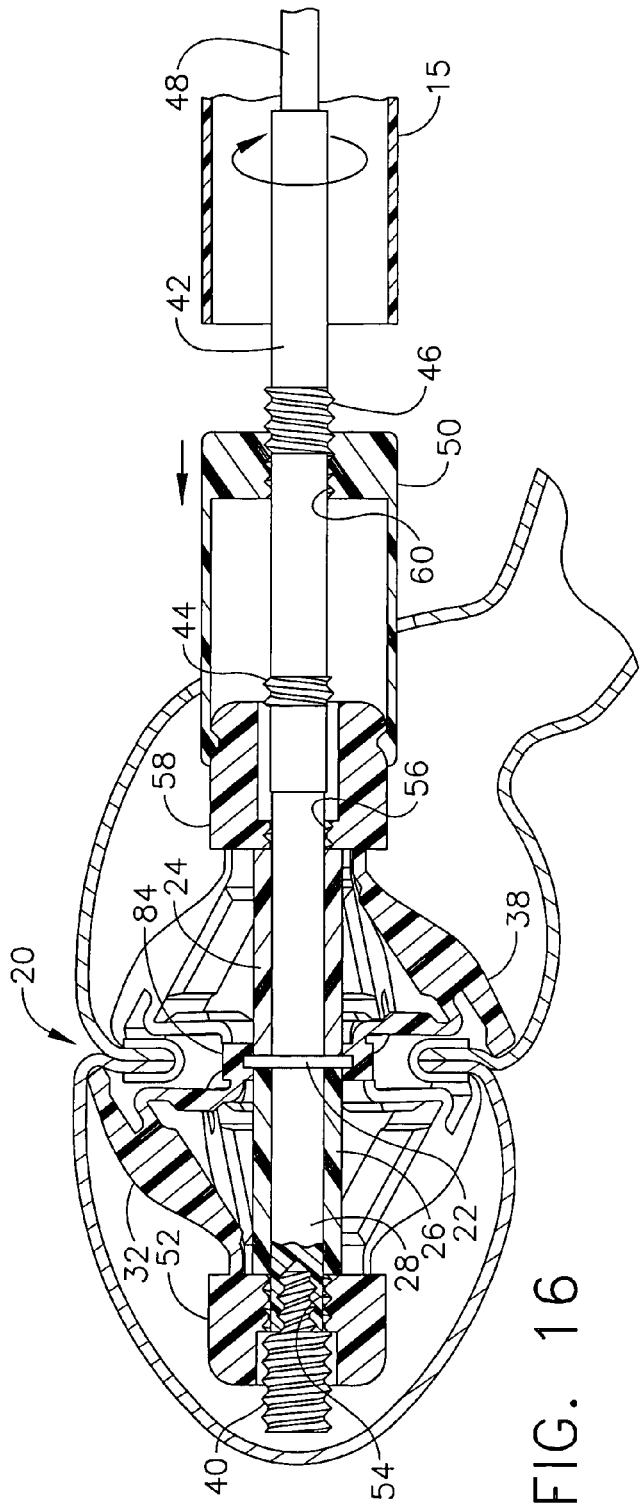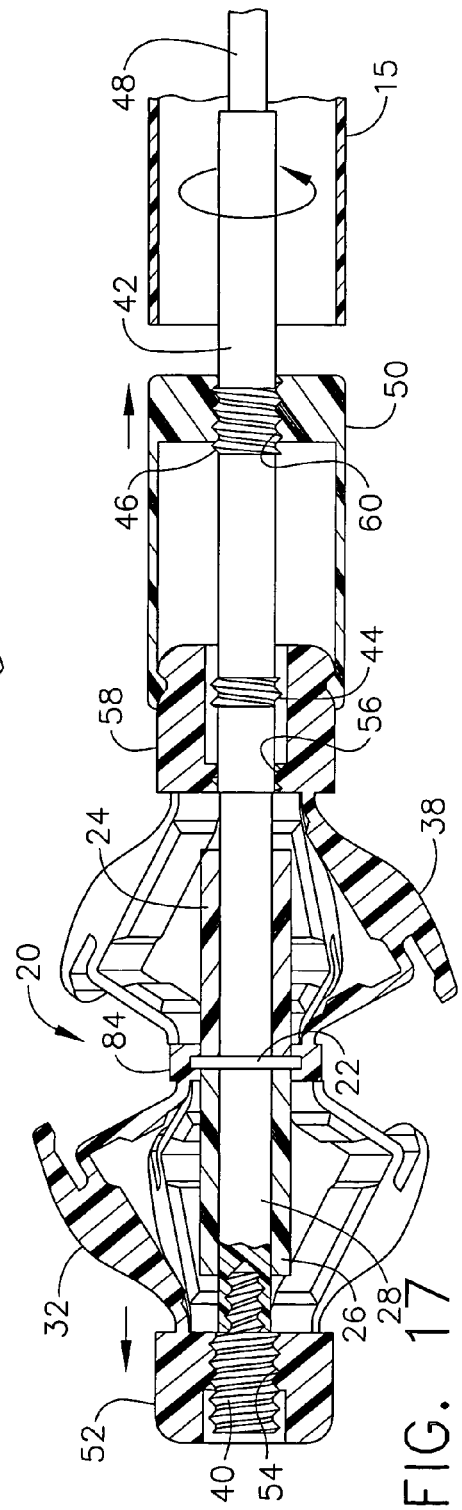
FIG. 16
FIG. 17

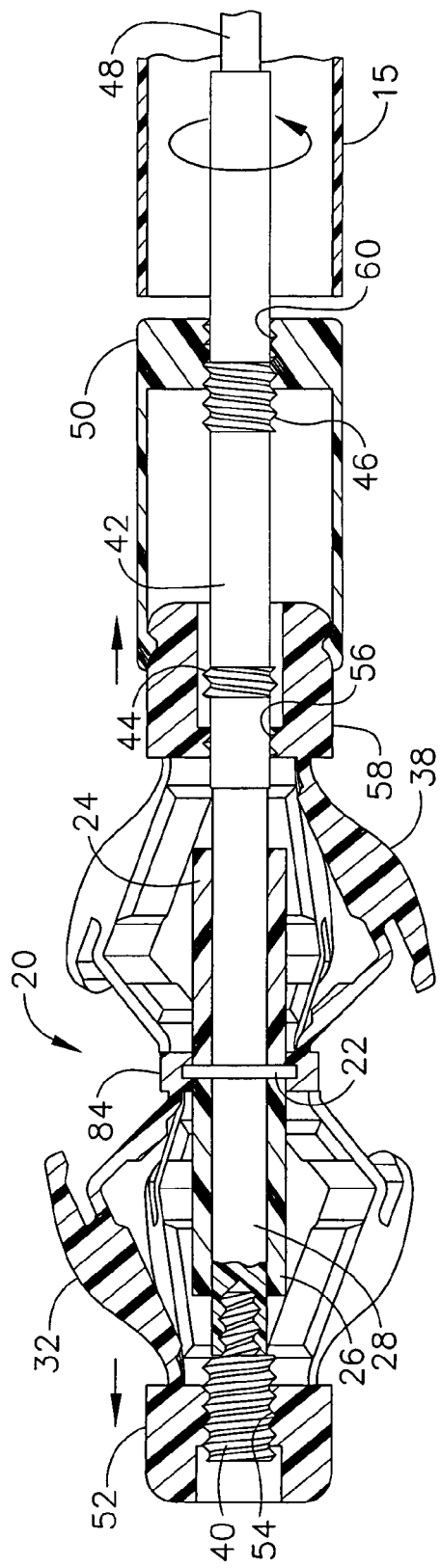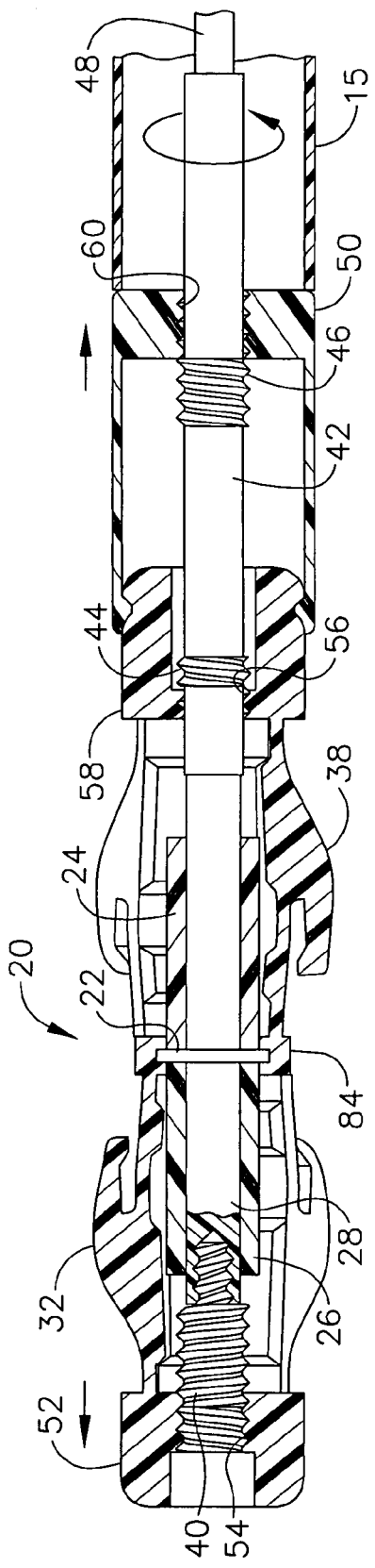

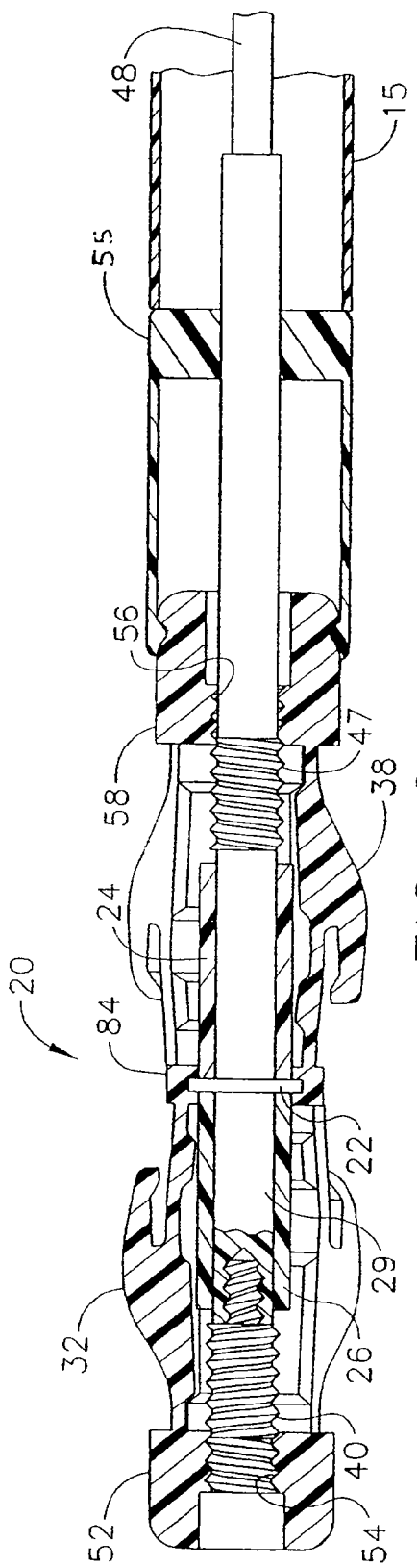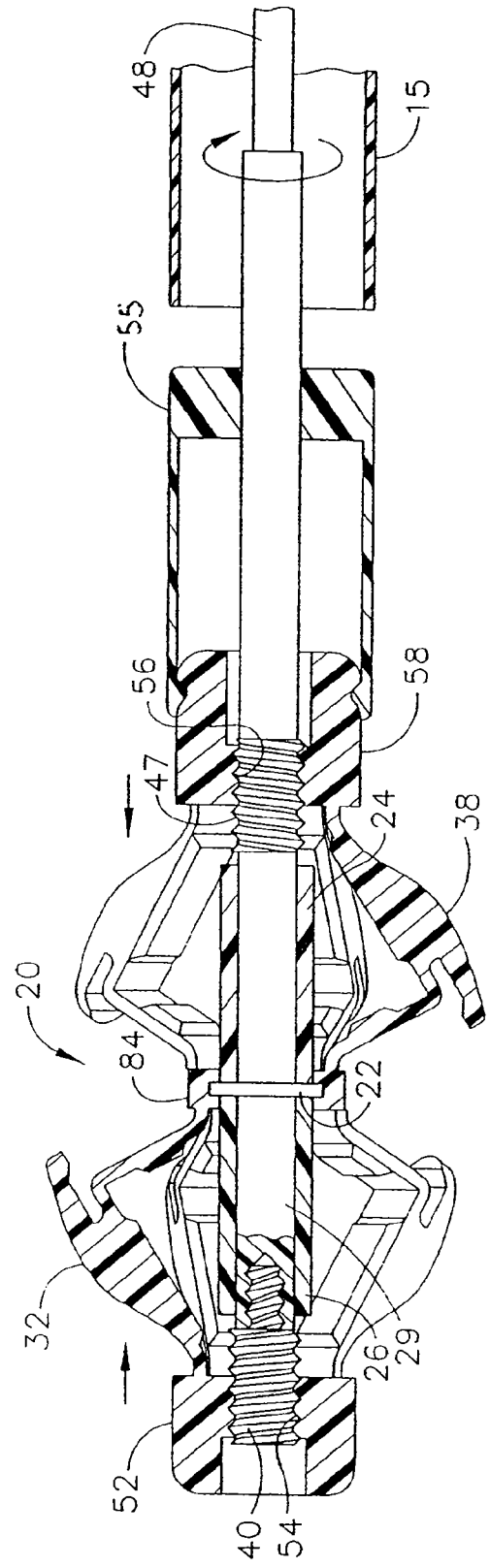

SCREW TIP CONTROL FOR ANASTOMOTIC RING APPLIER

FIELD OF THE INVENTION

The present invention relates, in general, to surgery and, more particularly, to a device for performing a surgical procedure on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

Some conventional flexible applier devices that employ force transmission through cables to control the ring deployment mechanism might present the undesirable potential for cable buckling or device straightening. Consequently, it may be desirable to have an applier that employs torsional force transfer, such as via one or more threaded members.

BRIEF SUMMARY OF THE INVENTION

Embodiments of the invention provide an anastomotic ring applier device that has a threaded shaft that is operable to transfer torsional force to a ring deployment mechanism, thereby effecting actuation of the ring deployment mechanism.

In one embodiment, a surgical instrument for applying an anastomotic ring device is provided, comprising a handle connected to a ring deployment mechanism by an elongated shaft. The ring deployment mechanism is configured to receive and deploy an anastomotic ring. The elongate shaft is configured to transfer a torsional actuating force from the handle to the ring deployment mechanism.

In another embodiment, an instrument comprises an actuating member configured to receive an anastomotic ring. The actuating member is moveable between a cylindrical unactuated position and a hollow rivet forming shape in response to one or more actuating forces. The instrument further comprises a handle including an actuation mechanism. The actuation mechanism is operable to produce at least one of the one or more actuating forces. The instrument further comprises an elongate shaft connecting the handle to the actuating member. The elongate shaft is operatively configured to transfer the at least one of the one or more actuating forces from the handle to the actuating member. The instrument further comprises at least one threaded member operable to communicate at least one of the one or more actuating forces to the actuating member.

In yet another embodiment, an instrument comprises an actuating member configured to receive an anastomotic ring. The actuating member is moveable between a cylindrical unactuated position and a hollow rivet forming shape in response to one or more linear actuating forces. The instrument further comprises a handle having an actuation mechanism that is operable to produce a torsional force. The instrument further comprises one or more translating members in communication with the actuating member. The one or more translating members are configured to translate the torsional force into the one or more linear actuating forces. The instrument further comprises an elongate shaft connecting the handle to the actuating member. The shaft has at least one transfer member that is operatively configured to transfer the torsional force to the translating member.

In still another embodiment, a method of deploying an anastomotic ring comprises positioning an anastomotic ring applier at an anastomosis site. The applier comprises a handle including an actuator that is operable to generate a torsional force. The applier further comprises a ring deployment mechanism comprising an anastomotic ring. The ring deployment mechanism is operable to deploy the anastomotic ring in response to one or more actuating forces. The applier further comprises a shaft connecting the handle to the ring deployment mechanism. The shaft comprises a torsion member that is operable to communicate the torsional force. The applier further comprises a translating member that is in communication with the ring deployment mechanism and the torsion member. The translating member is configured to translate the torsional force into the one or more actuating forces. The method further comprises manipulating the actuator to generate the torsional force. The method further comprises de-actuating the ring deployment mechanism and removing the applier from the anastomosis site.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

FIG. 10 is a cross-sectional view of the anastomotic ring deployment mechanism of the device of FIG. 1 in an unactuated position.

FIG. 11 is a cross-sectional view of the proximal portion of FIG. 9.

FIG. 12 is the anastomotic ring deployment mechanism of FIG. 10 with its distal portion in a partially actuated position.

FIG. 13 is the anastomotic ring deployment mechanism of FIG. 12, with an indication of pulling to engage threads.

FIG. 14 is the anastomotic ring deployment mechanism of FIG. 10 with its distal and proximal portions in a partially actuated position.

FIG. 15 is the anastomotic ring deployment mechanism of FIG. 14, with an indication of pulling to engage threads.

FIG. 16 is the anastomotic ring deployment mechanism of FIG. 10 with its distal and proximal portions in a fully actuated position.

FIG. 17 is the anastomotic ring deployment mechanism of FIG. 10 with its distal and proximal portions in a first partially de-actuated position.

FIG. 18 is the anastomotic ring deployment mechanism of FIG. 10 with its distal and proximal portions in a second partially de-actuated position.

FIG. 19 is the anastomotic ring deployment mechanism of FIG. 10 with its distal and proximal portions in a fully de-actuated position.

FIG. 21 is a cross-sectional view of the anastomotic ring deployment mechanism of an alternate anastomotic ring applier device in an unactuated position.

FIG. 22 is the anastomotic ring deployment mechanism of FIG. 21 in a partially actuated position.

DETAILED DESCRIPTION OF EMBODIMENTS OF THE INVENTION

Figure 1:
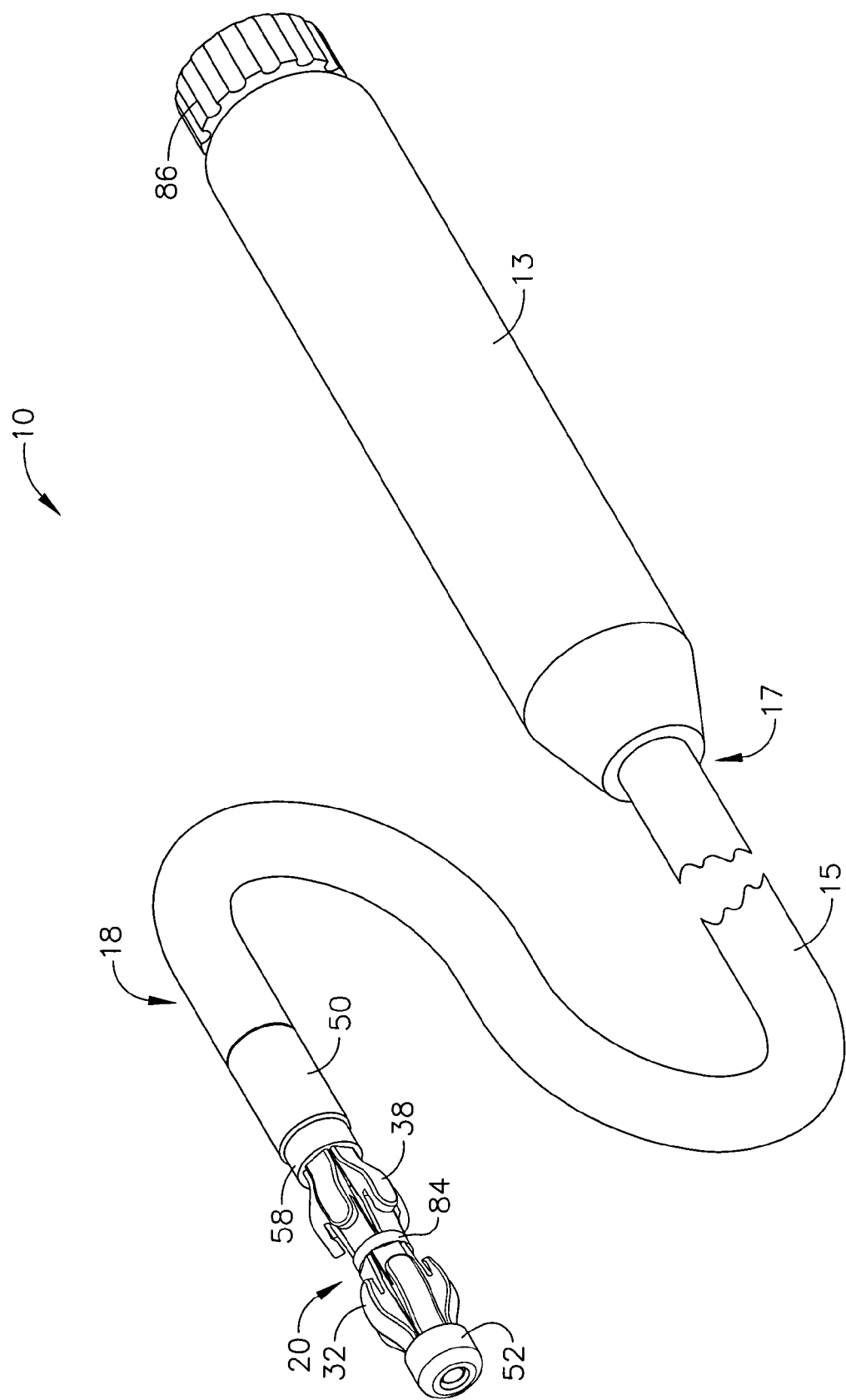
FIG. 1 is a perspective view of an anastomotic ring applier device.
Figure 2:
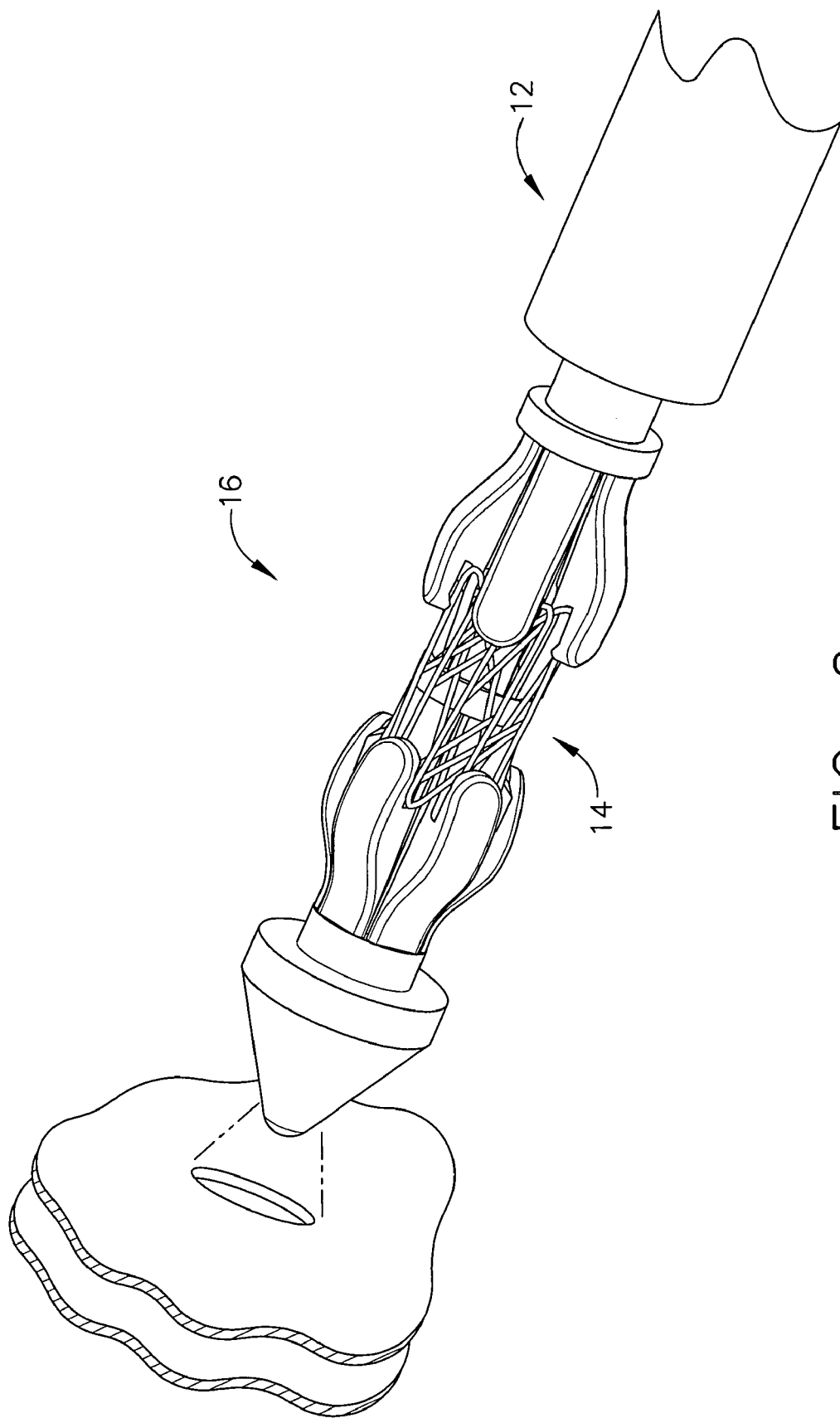
FIG. 2 is a partial perspective view of the distal portion of an anastomotic ring applier device holding an anastomotic ring in an unactuated position.
Figure 3:
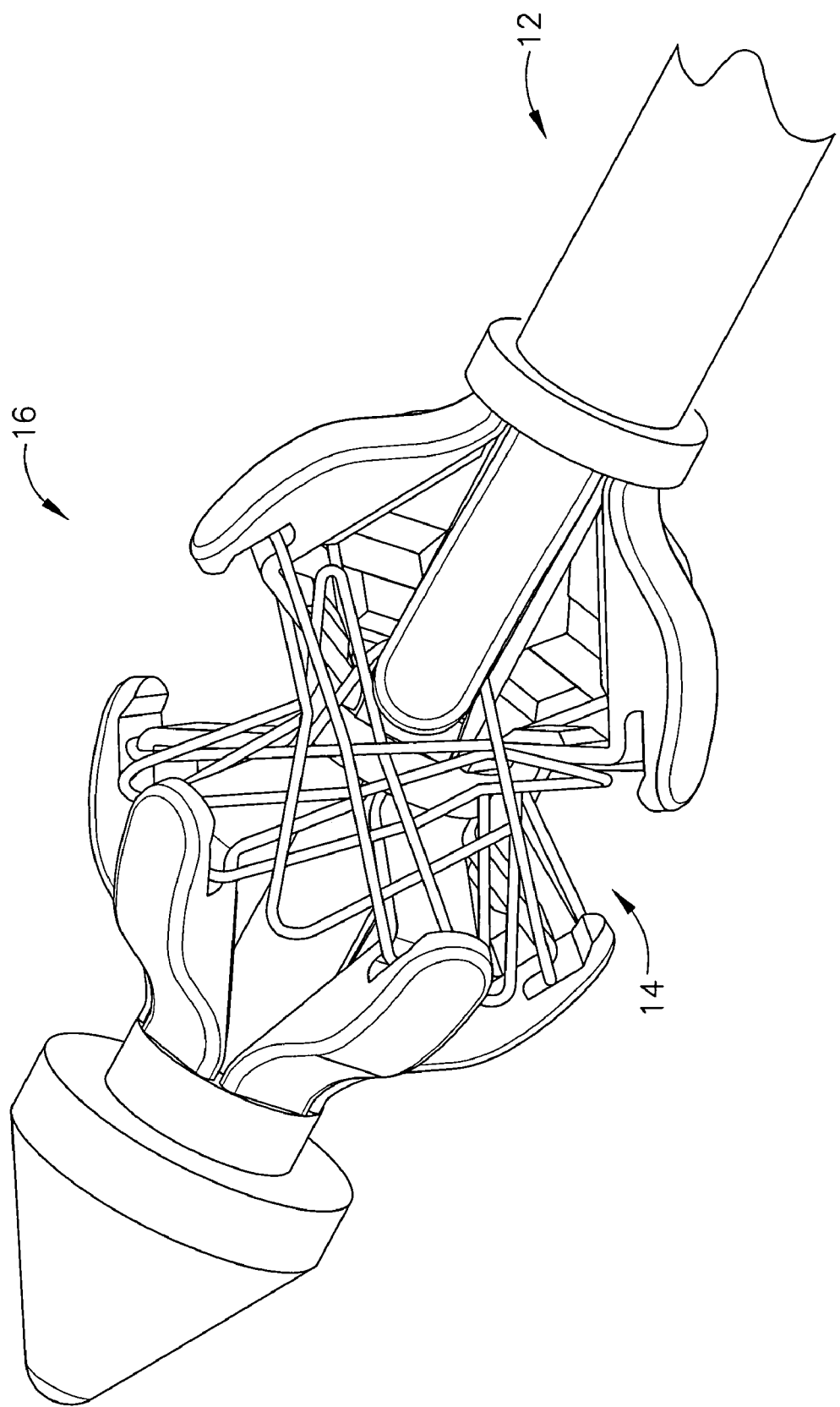
FIG. 3 is a partial perspective view of the distal portion of the device of FIG. 2 holding an anastomotic ring in the actuated position.
Figure 4:
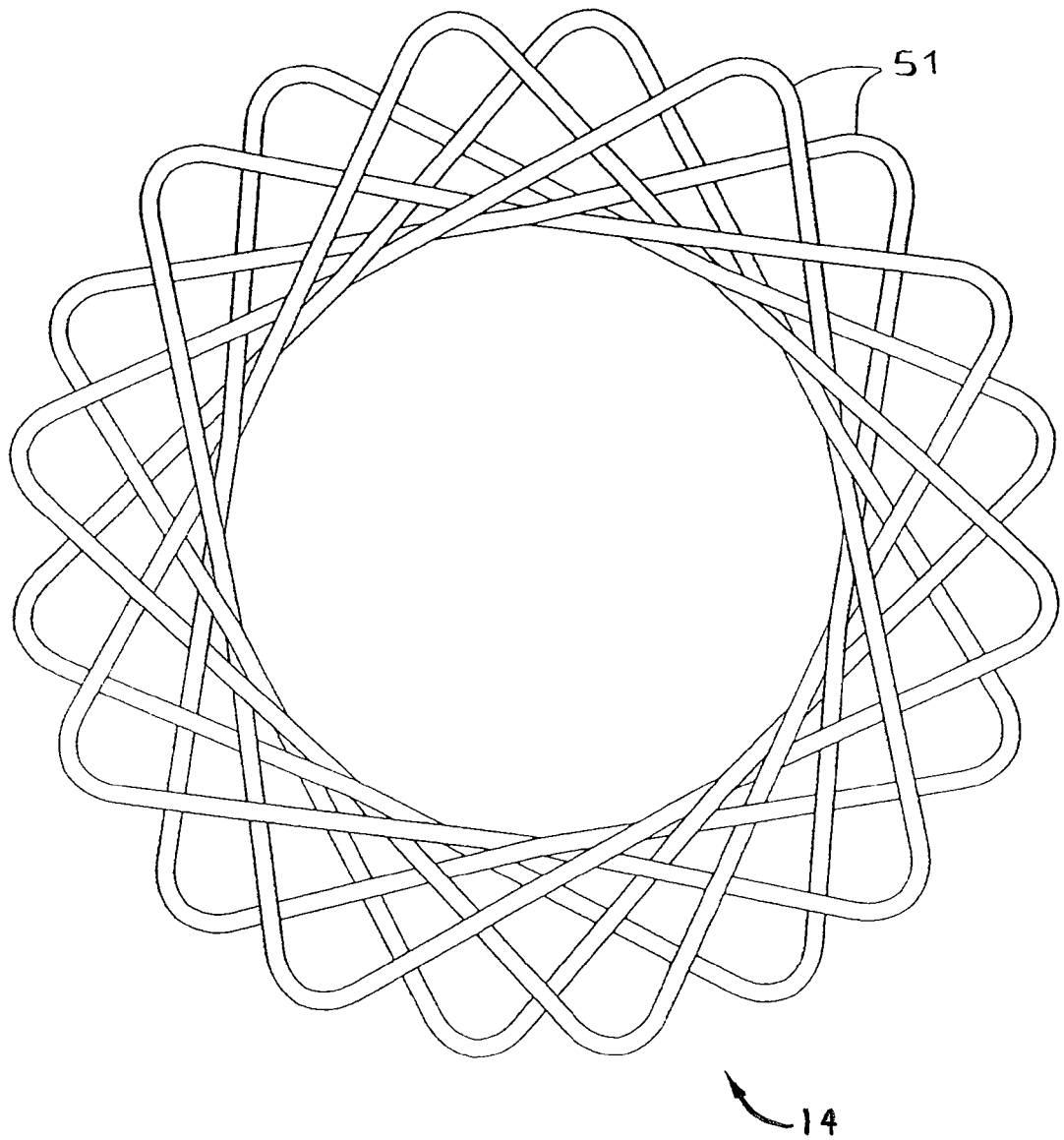
FIG. 4 is a frontal view of an actuated anastomotic ring.

Turning to the Drawings, wherein like numerals denote like components throughout the several views, FIG. 1 depicts an applier 10 that is operable to deploy and actuate an anastomotic ring device (not pictured in FIG. 1) from a generally cylindrical shape to one having properties of a hollow rivet, or ring, capable of forming an anastomotic attachment at an anastomosis target site, such as in a bariatric gastric bypass of a morbidly obese patient. FIG. 2 depicts another applier 12. It will be appreciated that appliers 10, 12 may be used in a variety of ways, including but not limited to laparoscopically or endoscopically. Applier 12 is shown in FIG. 2 with an anastomotic ring 14 on a deployment mechanism 16. In FIG. 2, anastomotic ring 14 is shown in the compressed, cylindrically-shaped position. In FIG. 3, deployment mechanism 16 of applier 12 has moved anastomotic ring 14 to the actuated, hollow rivet-shaped position. FIG. 4 is a close-up view of anastomotic ring 14 in the actuated position. Anastomotic ring 14 may comprise a shape memory effect (SME) material, such as nitinol by way of example only, that further assists in actuation to an engaging hollow rivet shape. Other suitable anastomotic ring 14 materials will be apparent to those of ordinary skill in the art. An exemplary anastomotic ring 14 is described in detail in U.S. Patent Application Publ. No. US 2003/0032967 to Park et al.

It will be appreciated that the terms "proximal" and "distal" are used herein with reference to a clinician gripping a handle of applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

Figure 5:
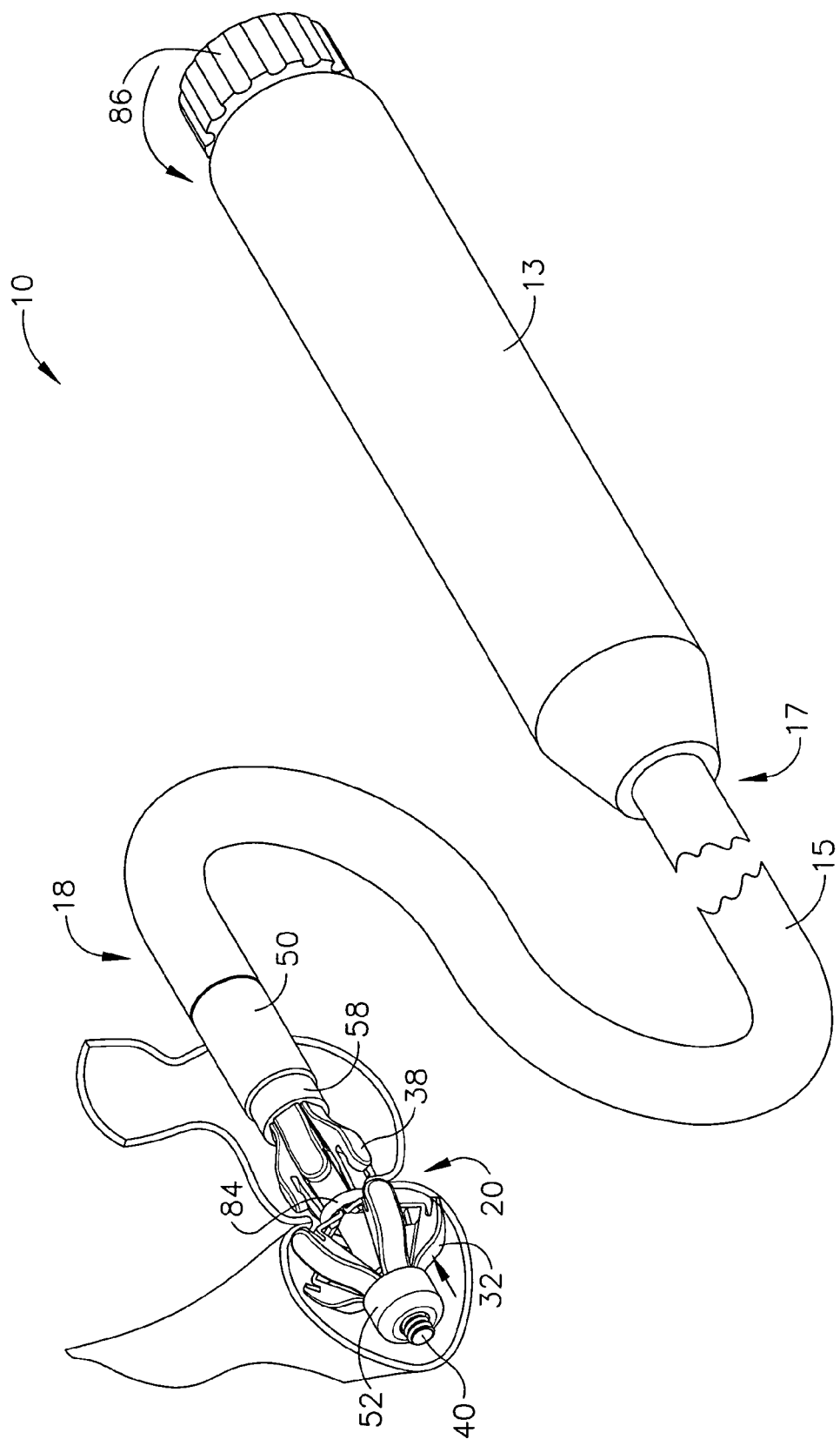
FIG. 5 is a perspective view of the anastomotic ring applier device of FIG. 1 with the distal portion of its ring deployment mechanism partially actuated.
Figure 6:
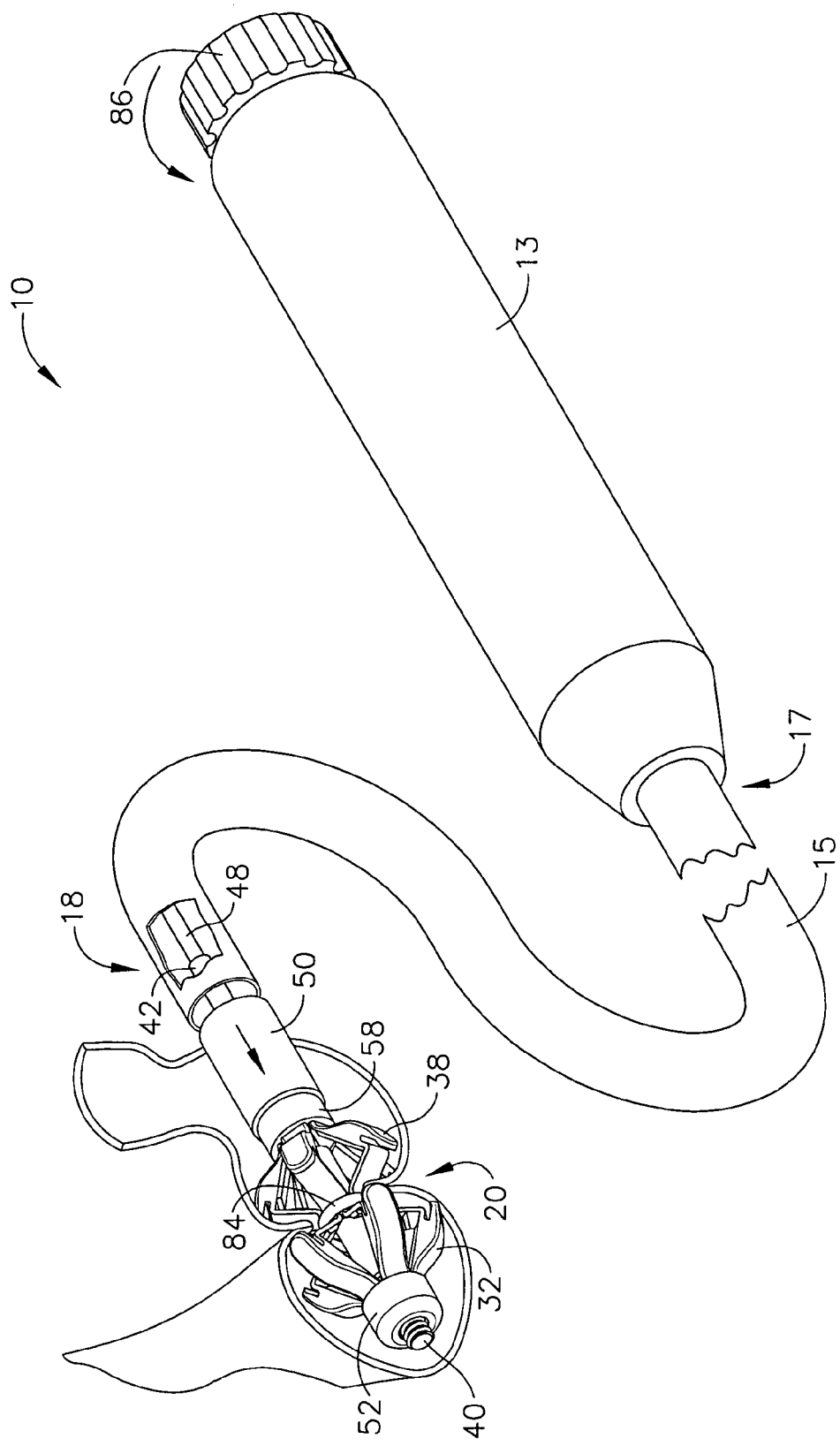
FIG. 6 is a perspective view of the device of FIG. 1 with both the distal portion and the proximal portion of its ring deployment mechanism partially actuated.

Referring to FIGS. 1, 5, and 6, applier 10 of the present example comprises a handle 13 connected to an elongated shaft 15. The elongated shaft 15 comprises a proximal portion 17 and a distal portion 18. Distal portion 18 has a ring deployment mechanism 20 connected thereto.

Figure 8:
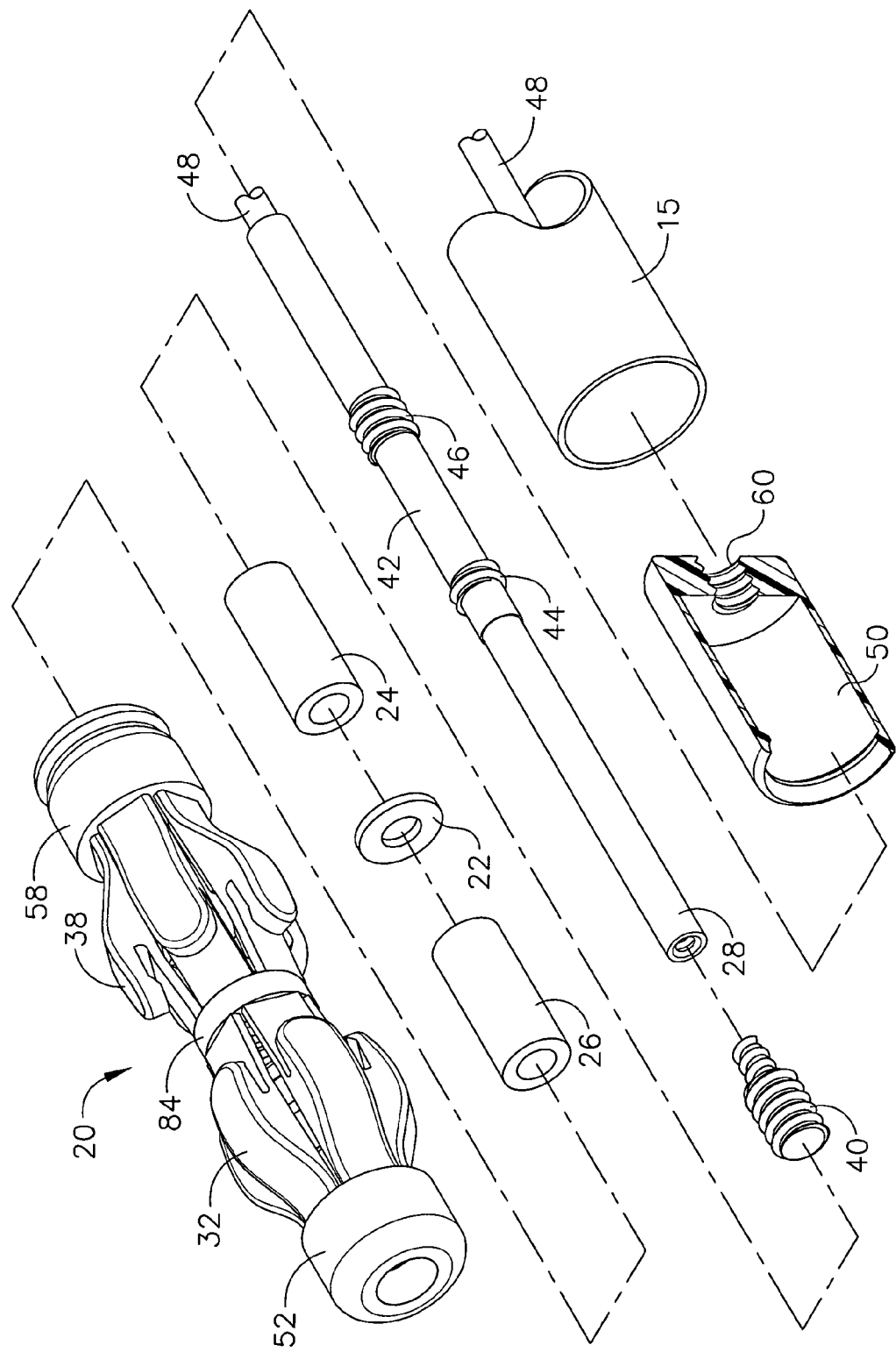
FIG. 8 is a perspective, exploded view of the anastomotic ring deployment mechanism of the device of FIG. 1.

FIG. 8 depicts an exemplary embodiment of ring deployment mechanism 20. As shown, ring deployment mechanism 20 comprises a plurality of distal fingers 32 joined to a distal ring member 52, a plurality of proximal fingers 38 joined to a proximal ring member 58, and a mid-ring 84 positioned between the distal ring member 52 and proximal ring member 58. Distal ring member 52 has a threaded opening 54 formed therein. Similarly, proximal ring member 58 has a threaded opening 56 formed therein.

Distal fingers 32 are in a double-hinged relationship with mid-ring 84, such that proximal motion of distal ring member 52 causes the tips of distal fingers 32 to articulate outwardly and deploy a distal portion of an anastomotic ring. Distal fingers 32 are configured to hold the distal portion of the anastomotic ring 14 by engaging petals 51 prior to and during deployment of the anastomotic ring 14, and release petals 51 upon deployment of the anastomotic ring 14. Similarly, proximal fingers 38 and mid-ring 84 are in a double-hinged relationship, such that distal motion of proximal ring member 58 causes the tips of proximal fingers 38 to articulate outwardly and deploy a proximal portion of an anastomotic ring 14. Proximal fingers 38 are configured to hold the proximal portion of the anastomotic ring 14 by engaging petals 51 prior to and during deployment of the anastomotic ring 14, and release petals 51 upon deployment of the anastomotic ring 14. In the illustrated version fingers 32, 38 each comprise a slot 37 and an inwardly directed tip 39 adjacent to the open end of each slot 37. Of course, any suitable alternative to fingers 32, 38 may be used to hold and/or deploy an anastomotic ring 14.

As shown in FIGS. 8, 10, 12-19, and 21-23, a grounding washer 22 is positioned within ring deployment mechanism 20. Washer 22 is fixed within mid-ring 84 to substantially constrain longitudinal movement of washer 22 relative mid-ring, though rotation of washer 22 may be possible relative mid-ring 84. A proximal sheath 24 is positioned adjacent to and proximal of washer 22, while a distal sheath 26 is positioned adjacent to and distal of washer 22. Ring deployment mechanism 20, washer 22, and sheaths 24, 26 are longitudinally positioned about rod 28. Rod 28 has a threaded end member 40 connected to its distal end, and threaded sleeve 42 connected to its proximal end. Threaded end member 40 is fixedly inserted into a threaded opening at the distal end of rod 28. It will be appreciated that threaded end member 40 and/or threaded sleeve 42 may be fixedly secured to rod 28 in any suitable way, including but not limited to the use of a permanent adhesive. Threaded sleeve 42 has a first thread set 44 and a second thread set 46 proximal of first thread set 44. As shown, the threads of first thread set 44 and the threads of second thread set 46 have a reversed orientation relative the threads of threaded end member 40.

The distal end of threaded sleeve 42 is fixedly connected to the proximal end of rod 28, while the proximal end of threaded sleeve 42 is fixedly connected to the distal end of a torsion member 48. Torsion member 48, threaded sleeve 42 (with thread sets 44, 46), rod 28, and threaded end member 40 are all thus configured to rotate unitarily. Torsion member 48 extends through shaft 15. In the present example, torsion member 48 comprises a cable. However, it will be appreciated that torsion member 48 may be of any other suitable form, such as a shaft by way of example only, or have any suitable features.

Pusher member 50 is joined to proximal ring member 58, and has a threaded opening 60 formed therein. In one embodiment, pusher member 50 is fixed to proximal ring member 58 such that rotation of pusher member 50 relative proximal ring member 58 is prevented. As shown in FIGS. 1, 5-7, and 12-19, pusher member 50 may abut the distal end of shaft 15, but is not fixedly attached thereto.

As used herein, the term "threaded member" shall be read to include anything that has one or more inclined threads formed therein or thereon. Accordingly, and by way of example only, threaded end member 40, distal ring member 52, proximal ring member 58, threaded sleeve 42, and pushing member 50 may all be regarded as "threaded members." It will be appreciated that threaded members are operatively configured to translate torsional forces into linear or longitudingal forces. Threaded members may thus be regarded as "translating members," which includes anything capable of translating torsional forces into linear or longitudinal forces. As used herein, the term "member," shall not be read to be limited to a singular piece or a homogenous continuum of material. In other words, a "member" may, but need not, comprise a plurality of parts joined together in any suitable way. Suitable examples of threaded members and translating members will be apparent to those of ordinary skill in the art.

It will be appreciated that, when torsion member 48 is rotated, friction between second thread set 46 and threaded opening 60 of pusher member 50 may urge pusher member 50 to rotate relative shaft 15. Similarly, friction between first thread set 44 and threaded opening 56 of proximal ring member 58, as well as friction between threaded end member 40 and threaded opening 54 of distal ring member 52, may urge ring deployment mechanism to rotate relative shaft 15 upon rotation of torsion member 48. Accordingly, it will be appreciated that one or more components or features may be added to distal portion 18 of shaft 15 and/or pusher member 50 to prevent rotation of pusher member 50 and ring deployment mechanism 20 relative shaft 15 when torsion member 48 is rotated. In one embodiment, such components permit at least some longitudinal movement of pusher member 50 relative shaft 15. Suitable components or features for preventing rotation while permitting longitudinal movement, or other ways to address the aforementioned friction if necessary or otherwise desired, will be apparent to those of ordinary skill in the art. Alternatively, normal or frictional forces exerted by adjacent tissue during use of applier 10 may suffice to overcome friction between threads 40, 44, 46 and openings 54, 56, 60 during rotation of torsion member 48.

Figure 9:
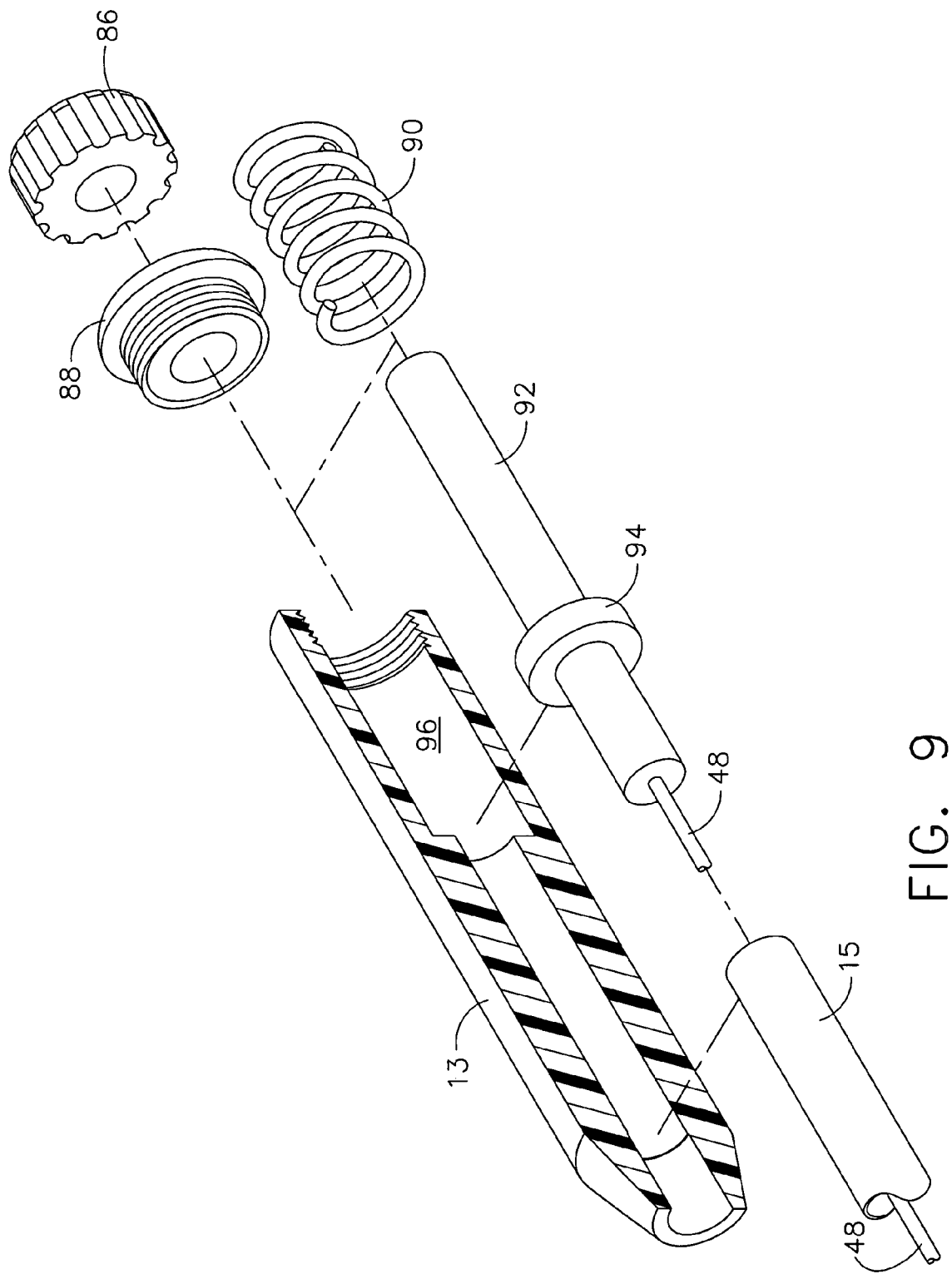
FIG. 9 is a perspective, cross-sectional exploded view of a proximal portion of the device of FIG. 1 with a left housing half omitted.
Figure 20:
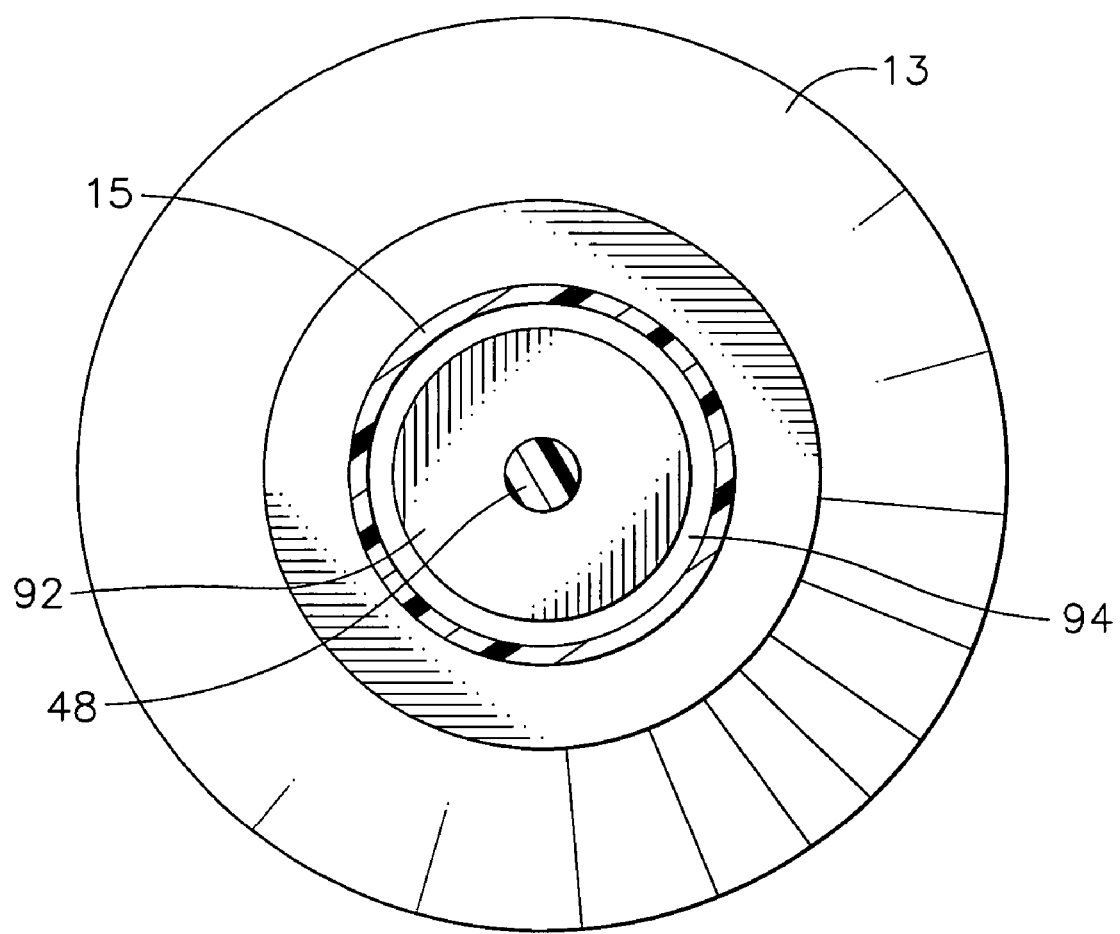
FIG. 20 is a cross-sectional view taken along Plane 20 of FIG. 11.

FIGS. 9, 11, and 20 show an exemplary handle 13 configuration, which may be used to effect rotation of torsion member 48. As shown, handle 13 comprises a knob 86, a screw cap 88, a spring 90, and a handle rod 92. Handle rod 92 has a circumferential flange 94. The proximal end of torsion member 48 terminates in the distal end of handle rod 92, and is fixedly secured therein, such that handle rod 92 and torsion member 48 are configured to rotate unitarily. Handle 13 further comprises a cylindrical cavity 96, which is sized to receive handle rod 92. Cylindrical cavity 96 has a radius that is approximately equal to the radius of flange 94, such that distal longitudinal movement of handle rod 92 will be prevented by engagement of flange 94 with the distal surface of cylindrical cavity 96. The proximal end of cylindrical cavity 96 is threaded to receive screw cap 88. Handle rod 92 has a length that is greater than the length of cylindrical cavity 96, such that a proximal portion of handle rod 92 will protrude from handle 13 with handle rod 92 disposed therein. Screw cap 88 has an opening through which this proximal portion of handle rod 92 may pass. Spring 90 is sized to fit in cylindrical cavity 96 between flange 94 and screw cap 88, with a bias to expand.

Knob 86 is fixedly secured to a protruding portion of handle rod 92. It will be appreciated that knob 86 may be used to generate a torsional force. Of course, a variety of alternatives for generating a torsional force exist, including but not limited to cranks, motors, and the like. Still other suitable members operable to generate a torsional force will be apparent to those of ordinary skill in the art. In this embodiment, rotation of knob 86 will cause rotation of torsion member 48. Of course, a variety of alternative handle 13 configurations may be used to effect rotation of torsion member 48, most of which, if not all, will be apparent to those of ordinary skill in the art.

In use, applier 10, loaded with anastomotic ring 14, is positioned at an anastomosis site in a patient while ring deployment mechanism 20 is in an unactuated configuration. An exemplary unactuated configuration is shown in FIGS. 1 and 10 (anastomotic ring 14 omitted). With applier 10 properly positioned, knob 86 is rotated clockwise, which will cause handle rod 92, torsion member 48, threaded sleeve 42, rod 28, and threaded end member 40 to rotate clockwise unitarily therewith. During this initial rotation, threaded end member 40 will engage with threaded opening 54 in distal ring member 52, thereby driving distal ring member 52 proximally relative threaded end member 40. Upon full passage of threaded end member 40 through threaded opening 54, ring deployment mechanism 20 will reach a first partially actuated configuration. An exemplary first partially actuated configuration is shown in FIGS. 5 and 12.

In the next stage of use, the user pulls knob 86 proximally, which will cause pulling of threaded sleeve 42 and the aforementioned components in between. As shown in FIG. 13, where pushing member 50 is abutting the distal end of shaft 15, such pulling will further cause engagement of first thread set 44 with threaded opening 56 of proximal ring member 58. Knob 86 is then again rotated clockwise, which will cause rotation of threaded sleeve 42 and the aforementioned components in between. Of course, knob 86 may be pulled proximally and rotated clockwise concomitantly. During the rotation of first thread set 44 while first thread set 44 is engaged with threaded opening 56, first thread set 44 will drive proximal ring member 58 distally relative first thread set 44. Upon full passage of first thread set 44 through threaded opening 56, ring deployment mechanism 20 will reach a second partially actuated configuration. An exemplary second partially actuated configuration is shown in FIGS. 6 and 14. As shown, pushing member 50 no longer abuts the distal end of shaft 15 when ring deployment mechanism 20 has reached the second partially actuated configuration. While not shown, it will be appreciated that a ring-like seal may be provided at the distal end of shaft 15 to prevent material from entering the otherwise open distal end of shaft 15 when ring deployment mechanism 20 has reached the second partially actuated configuration.

Figure 7:
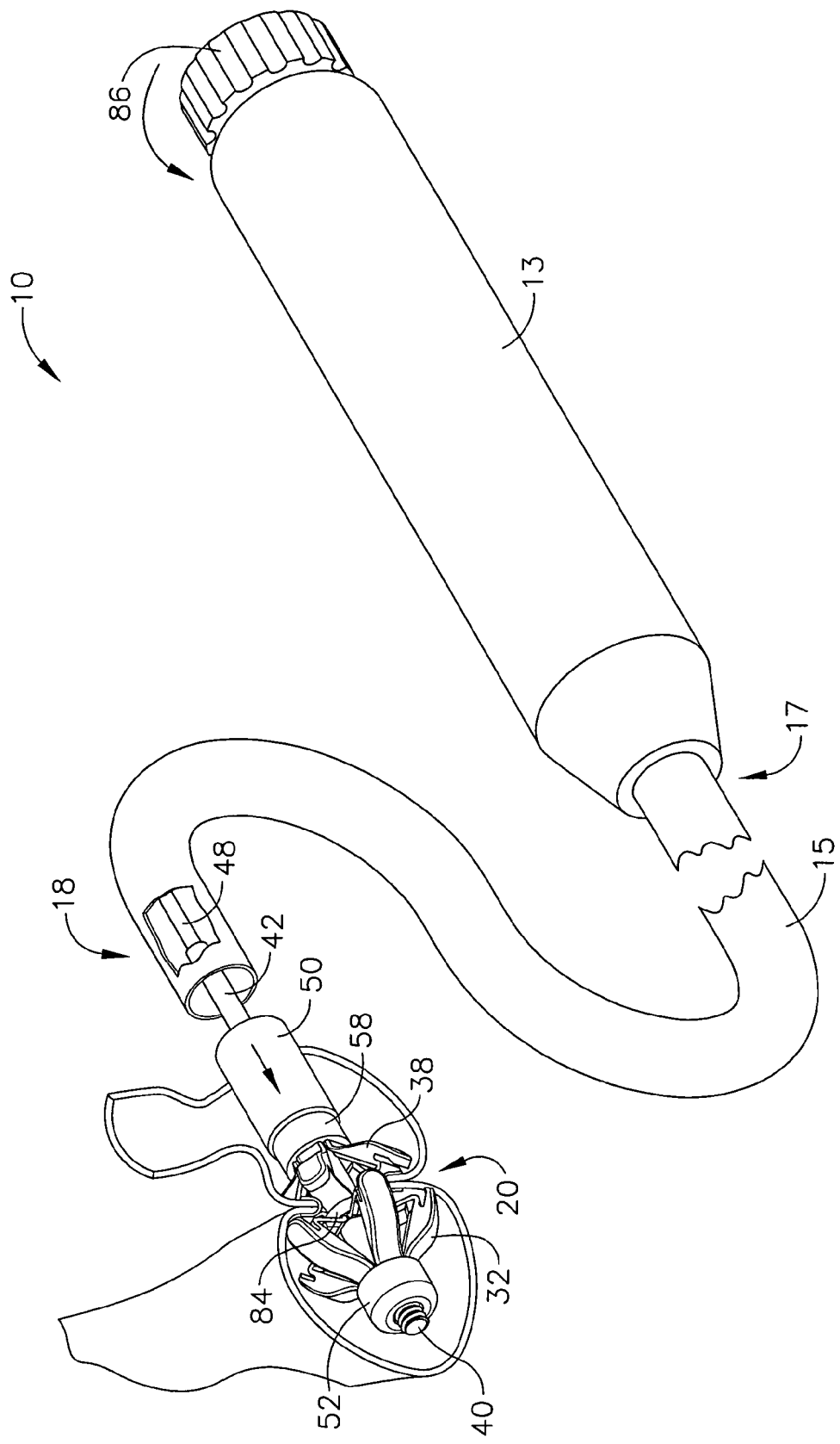
FIG. 7 is a perspective view of the device of FIG. 1 with both the distal portion and the proximal portion of its ring deployment mechanism fully actuated.

In the next stage of use, the user again pulls knob 86 proximally, which will cause pulling of threaded sleeve 42 and the aforementioned components in between. As shown in FIG. 15, this further causes pushing member 50 to again abut the distal end of shaft 15, and will also lead to engagement of second thread set 46 with threaded opening 60 of pushing member 50. Knob 86 is then again rotated clockwise, which will cause rotation of threaded sleeve 42 and the aforementioned components in between. Of course, knob 86 may be pulled proximally and rotated clockwise concomitantly. During the rotation of second thread set 46 while second thread set 46 is engaged with threaded opening 60, second thread set 46 will drive pushing member 50 distally relative second thread set 46. This driving will cause ring deployment mechanism 20 will reach a fully actuated configuration. An exemplary fully actuated configuration is shown in FIGS. 7 and 16.

It will be appreciated that, during or between any of the above-mentioned stages of deployment, and particularly between the second partially actuated configuration and the fully actuated configuration, either the distal sheath 26 or the proximal sheath 24 will come into contact with the distal ring member 52 or the proximal ring member 58 (respectively) before the other sheath 26, 24 comes into contact with its respective ring member 52, 58. The presence of the sheaths 26, 24 will thus prevent further actuation of respective fingers 32, 38, and will ensure that each set of fingers 32, 38 will ultimately reach an approximately equal level of actuation by the time ring deployment mechanism 20 reaches the fully actuated configuration. Sheaths 26, 24 will also prevent "over-actuation" of fingers 32, 38. In addition, when sheaths 26, 24 are both engaged with respective ring members 52, 58, further rotation of knob 86 and all unitary distal components 92, 48, 42, 28, 40 will be prevented, thereby providing tactile feedback to the user indicating that the ring deployment mechanism 20 has reached a full actuated configuration. Of course, any other features or components may be used as an alternative to sheaths 26, 24 for providing limitation of actuation and/or tactile feedback.

Upon ring deployment mechanism 20 having reached a fully actuated configuration, and the resulting deployment of an anastomotic ring 14, the applier 10 may be extracted from the patient in a reversal of several of the foregoing steps. In other words, applier 10 may be extracted after "de-actuation" of the ring deployment mechanism 20. As used herein, the term "de-actuation" and its variants should be understood as referring to a process whereby the ring deployment mechanism 20 is brought from a fully actuated configuration to an unactuated configuration. A "de-actuated" configuration is thus a species of unactuated configuration, whereby the ring deployment mechanism 20 has previously been placed in a fully actuated configuration. As shown in FIG. 17, de-actuation of the ring deployment mechanism 20 may be effected through counterclockwise rotation of knob 86. Such rotation will cause second thread set 46 to drive pushing member 50 proximally. It will also be appreciated that, in the present example, the resilience of the material comprising ring deployment mechanism 20 will urge threaded opening 54 of distal ring member 53 into engagement of threaded end member 40, whereby rotation of threaded end member (effected via knob 86) will drive distal ring member 53 distally. As pushing member 50 and proximal ring member 58 are driven proximally, while distal ring member 52 is driven distally, ring deployment mechanism 20 will approach a de-actuated configuration. Intermediate stages of such de-actuation are shown in FIGS. 17-18, while a fully de-actuated configuration is shown in FIG. 19. Applier 10 may be withdrawn from the patient upon full de-actuation of ring deployment mechanism 20.

It will be appreciated that several of the foregoing features, components, and steps may be varied. By way of example only, threads of threaded end member 40, first thread set 44, and second thread set 46 may be configured such that actuation is effected through counterclockwise rotation of knob 86, with de-actuation effected through clockwise rotation of knob 86. In addition, threads of threaded end member 40, first thread set 44, and second thread set 46 and/or respective threaded openings 54, 56, 60 may be spaced such that proximal pulling of knob 86 during actuation is not necessary. Still other variations will be apparent to those of ordinary skill in the art.

Figure 23:
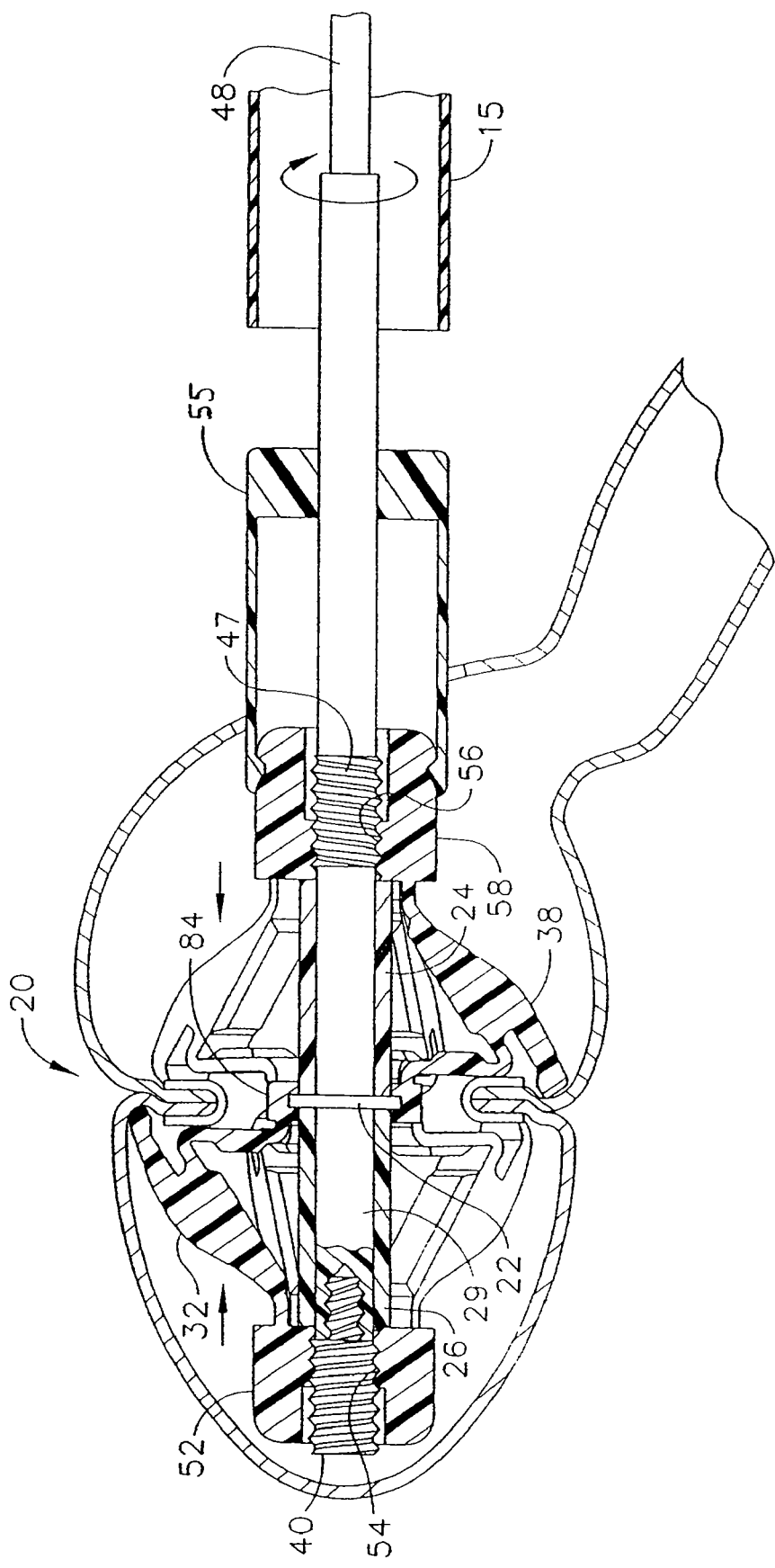
FIG. 23 is the anastomotic ring deployment mechanism of FIG. 21 in a fully actuated position.

An applier 10 is shown in FIGS. 21-23 having an alternate pusher member 55 and an alternate rod 29. Alternate pusher member 55 is similar to pusher member 60 except that alternate pusher member 55 lacks threaded opening 60. It will be noted that in this embodiment, threaded sleeve 42 is also absent. Instead, alternate rod 29 has an alternate thread set 47 formed thereon, in addition to having threaded end member 40 screwably inserted in its distal end. Thus, alternate rod 29 is a threaded member. As shown, the threads of alternate thread set 47 have a reversed orientation relative the threads of threaded end member 40. Alternate thread set 47 is configured to engage threaded opening 56 of proximal ring member 58.

In the embodiment depicted in FIG. 21, applier 10 is in an unactuated configuration. While in this configuration, a portion of threaded end member 40 is engaged with a portion of threaded opening 54 of distal ring member 52. Similarly, while applier 10 is in the unactuated configuration, a portion of alternate thread set 47 is engaged with a portion of proximal ring member 58. As with embodiments discussed above, when knob 86 is turned, torsion member 48 rotates unitarily therewith. Since torsion member 48 is fixedly coupled with alternate rod 29, alternate rod 29, alternate thread set 47, and threaded end member 40 will also rotate unitarily with knob 86.

As shown in FIG. 22, which depicts an intermediate stage of ring deployment mechanism 20 actuation, clockwise rotation of knob 86 will effect simultaneous proximal movement of distal ring member 52 and distal movement of proximal ring member 58. Upon sufficient rotation of knob 86, ring deployment mechanism 20 will reach a stage of full actuation, which is shown in FIG. 23. As with previously-discussed embodiments, sheaths 26, 24 prevent "over-actuation" of ring deployment mechanism 20, while also providing tactile feedback of full actuation by preventing further rotation of knob 86. Applier 10 of this example may be placed in a de-actuated configuration simply by rotating knob 86 in the opposite direction (counterclockwise in the present example). It will be appreciated that, in the embodiment depicted in FIGS. 21-23, the user need not pull knob 86 proximally during actuation of ring deployment mechanism 20.

In yet another embodiment, torsion member 48 extends all the way through distal ring member 52, and has at least two threaded portions formed thereon in place of threaded end member 40 and thread sets 44, 46, 47. Still other variations will be apparent to those of ordinary skill in the art.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A surgical instrument operable to implant an anastomotic ring device, the instrument comprising:
    (a) a handle;
    (b) a ring deployment mechanism configured to receive and deploy an anastomotic ring, wherein the ring deployment mechanism comprises a plurality of fingers, a distal ring member, a proximal ring member, and a mid-ring, wherein the plurality of fingers comprises a first set of fingers and a second set of fingers, wherein each of the plurality of fingers comprises a distal end, a proximal end, and a hinge positioned longitudinally between the distal end and the proximal end of each finger, wherein the first set of fingers and the second set of fingers are positioned about a common axis, wherein each of the first set of fingers terminate at the distal ring member at the distal end and terminate at the mid-ring at the proximal end, wherein each of the second set of fingers terminate at the proximal ring member at the proximal end and terminate at the mid-ring at the distal end, wherein each of the plurality of fingers are operable to articulate outwardly at the hinge from an unactuated position toward an actuated position; wherein the first set of fingers is operable to achieve the actuated position while the second set of fingers remains in the unactuated position, wherein the second set of fingers is operable to achieve the actuated position while the first set of fingers remains in the unactuated position; and
    (c) an elongate shaft connecting the handle to the ring deployment mechanism, wherein the elongate shaft is configured to transfer a torsional actuating force from the handle to the ring deployment mechanism, wherein the elongate shaft comprises a longitudinal axis;
    wherein each of the plurality of fingers comprises a slot, wherein each slot comprises an open end longitudinally opposed to a closed end, the open end of each slot is oriented in a longitudinal direction substantially parallel to the longitudinal axis of the elongate shaft when the ring deployment mechanism is in an unactuated position, wherein each of the plurality of fingers further comprises an inwardly directed tip adjacent to the open end of each slot.

2. The instrument of claim 1, wherein the handle comprises a knob, wherein the knob is operable to generate the torsional actuating force.

3. The instrument of claim 1, wherein the mid-ring is positioned about the common axis and between the first set of fingers and the second set of fingers.

4. The instrument of claim 1, wherein the shaft comprises at least one torsion member operable to communicate the torsional actuating force through the shaft.

5. The instrument of claim 4, wherein the torsion member is in communication with a rod, wherein the rod is in communication with the ring deployment mechanism.

6. The instrument of claim 5, wherein the rod comprises one or more sets of threads.

7. The instrument of claim 6, wherein at least one of the one or more sets of threads is configured to communicate the torsional actuating force to the ring deployment mechanism.

8. The instrument of claim 7, wherein the ring deployment mechanism is operable to deploy an anastomotic ring in response to the torsional actuating force.

9. The instrument of claim 6, further comprising at least one threaded member in communication with the rod.

10. The instrument of claim 1, wherein the ring deployment mechanism further comprises a grounding washer, wherein the grounding washer is substantially fixed within the mid-ring.

11. The instrument of claim 10, wherein the ring deployment mechanism further comprises a distal sheath and a proximal sheath, wherein the distal sheath is positioned along the common axis adjacent to and distal of the grounding washer, wherein the proximal sheath is positioned along the common axis adjacent to and proximal of the grounding washer, wherein the distal sheath is configured to engage the distal ring member upon complete actuation of the first set of fingers, wherein the proximal sheath is configured to engage the proximal ring member upon complete actuation of the second set of fingers, wherein further actuation of the fingers is prevented by the engagement of the distal ring member by the distal sheath and engagement of the proximal ring member by the proximal sheath, thereby providing tactile feedback to a user that the ring deployment mechanism has reached complete actuation.

12. The instrument of claim 1, the instrument further comprising
    (a) a first threaded member operable to communicate the torsional actuating force to the ring deployment mechanism, wherein the first threaded member comprises at least two sets of threads, wherein the at least two sets of threads comprise a plurality of threads having a first pitch orientation; and
    (b) a second threaded member operable to communicate the torsional actuating force to the ring deployment mechanism, wherein the second threaded member comprises at least one set of threads, wherein the at least one set of threads comprises a plurality of threads having a second pitch orientation, wherein the second pitch orientation is opposite relative to the first pitch orientation;
    wherein the at least two sets of threads of the first threaded member and the at least one set of threads of the second threaded member share a common axis with the first set of fingers and the second set of fingers, wherein the at least two sets of threads of the first threaded member are configured to translate the torsional actuating force into a distally-oriented longitudinal force, wherein the at least one set of threads of the second threaded member is configured to translate the torsional actuating force into a proximally-oriented longitudinal force.

13. The instrument of claim 12, wherein the at least two sets of threads of the first threaded member are configured to produce distal movement of the proximal ring member in response to the torsional actuating force, wherein the at least one set of threads of the second threaded member is configured to produce proximal movement of the distal ring member in response to the torsional actuating force, wherein distal movement of the proximal ring member urges the second set of fingers from the unactuated position toward the actuated position, wherein proximal movement of the distal ring member urges the first set of fingers from the unactuated position toward the actuated position.

14. A surgical instrument operable to implant an anastomotic ring, the instrument comprising:
    (a) an actuating member configured to receive an anastomotic ring, wherein the actuating member is moveable between a cylindrical, unactuated position and a hollow rivet forming shape in response to one or more actuating forces, wherein the actuating member comprises a distal ring member and a proximal ring member positioned longitudinally along a common axis, wherein the proximal ring member comprises a threaded opening;

(b) a handle including an actuation mechanism operable to produce at least one of the one or more actuating forces, wherein actuation of the actuation mechanism in a first direction produces a torsional actuating force oriented in a first rotational direction;

(c) an elongate shaft connecting the handle to the actuating member and operatively configured to transfer the at least one of the one or more actuating forces from the handle to the actuating member, wherein the elongate shaft comprises a distal end;

(d) a pusher member, wherein the pusher member comprises a proximal end and a distal end, wherein the distal end of the pusher member is fixedly attached to the proximal ring member such that proximal ring member and pusher member travel unitarily when traveling in a longitudinal direction, wherein the pusher member further comprises a threaded opening in the proximal end of the pusher member, wherein the proximal end of the pusher member is configured to abut the distal end of the elongate shaft, but is not fixedly attached thereto;

(e) a first threaded member operable to communicate at least one of the one or more actuating forces to the actuating member, wherein the first threaded member comprises at least two sets of threads, wherein the at least two sets of threads comprise a plurality of threads having a first pitch orientation, wherein the at least two sets of threads comprise a proximal set of threads and a distal set of threads, wherein the proximal set of threads is configured to engage the threaded opening in the proximal end of the pusher member, wherein the distal set of threads is configured to engage the threaded opening in the proximal ring member; and (f) a second threaded member operable to communicate at least one of the one or more actuating forces to the actuating member, wherein the second threaded member comprises at least one set of threads, wherein the at least one set of threads comprises a plurality of threads having a second pitch orientation, wherein the second pitch orientation is opposite relative to the first pitch orientation;

wherein the at least two sets of threads of the first threaded member and the at least one set of threads of the second threaded member are positioned longitudinally about a common axis, wherein the at least two sets of threads of the first threaded member are configured to translate the torsional actuating force created by actuation of the actuation mechanism in the first direction into a distally-oriented longitudinal force, wherein the at least one set of threads of the second threaded member is configured to translate the torsional actuating force created by actuation of the actuation mechanism in the first direction into a proximally-oriented longitudinal force, wherein the actuating member is configured to actuate in response to the distally-oriented and proximally-oriented longitudinal forces, wherein the at least two sets of threads of the first threaded member are configured to produce distal movement of the proximal ring member in response to the torsional force oriented in the first rotational direction; wherein the at least one set of threads of the second threaded member is configured to produce proximal movement of the distal ring member in response to the torsional force oriented in the first rotational direction.

15. The instrument of claim 14, wherein the actuating member further comprises a distal section and a proximal section, wherein the distal section is operable to actuate independently of the proximal section, wherein the proximal section is operable to actuate independently of the distal section.

16. A surgical instrument operable to implant an anastomotic ring, the instrument comprising:

(a) an actuating member configured to receive an anastomotic ring, wherein the actuating member is moveable between a cylindrical, unactuated position and a hollow rivet forming shape in response to one or more linear actuating forces, wherein the actuating member comprises a distal ring member and a proximal ring member positioned longitudinally along a common axis, wherein the distal ring member comprises a threaded opening extending axially through the distal ring member, wherein the proximal ring member comprises a threaded opening extending axially through the proximal ring member, wherein the actuating member further comprises a distal set of fingers, a proximal set of fingers, and a mid-ring member positioned along the common axis of the distal ring member and the proximal ring member, wherein the mid-ring member is positioned longitudinally between the distal ring member and the proximal ring member, wherein each finger of the distal set of fingers and each finger of the proximal set of fingers comprises a distal end, a proximal end, and a hinge positioned longitudinally between the distal end and the proximal end of each finger, wherein the distal end of each finger of the distal set of fingers is fixed to the distal ring member, wherein the proximal end of each finger of the distal set of fingers is fixed to the mid-ring member, wherein the distal end of each finger of the proximal set of fingers is fixed to mid-ring member, wherein the proximal end of each finger of the proximal set of fingers is fixed to the proximal ring member;

(b) a handle including an actuation mechanism operable to produce a torsional force;

(c) one or more translating members in communication with the actuating member, the one or more translating members being configured to translate the torsional force into the one or more linear actuating forces;

(d) an elongate shaft connecting the handle to the actuating member and having at least one transfer member operatively configured to transfer the torsional force to the translating member;

(e) a first set of threads and a second set of threads positioned longitudinally along a common axis, wherein the first set of threads comprises a plurality of threads having a first pitch orientation, wherein the second set of threads comprises a plurality of threads having a second pitch orientation, wherein the first pitch orientation is reversed relative to the second pitch orientation, wherein the first set of threads engages the threaded opening in the distal ring member, wherein the second set of threads engages the threaded opening in the proximal ring member, wherein the first set of threads and the second set of threads are configured to produce proximal movement of the distal ring member and distal movement of the proximal ring member, respectively, in response to the torsional force; and (f) a distal sheath comprising a tubular member having a proximal end and a distal end, wherein the distal sheath is positioned along the common axis of the distal ring member and the proximal ring member adjacent to and distal of the mid-ring member, wherein, upon complete actuation of the distal set of fingers, the distal end of the distal sheath abuts the distal ring member and the proximal end of the distal sheath abuts the mid-ring member; and (g) a proximal sheath comprising tubular member having a proximal end and a distal end, wherein the proximal sheath is positioned along the common axis of the distal ring member and the proximal ring member adjacent to and proximal of the mid-ring member, wherein, upon complete actuation of the proximal set of fingers, the proximal end of the proximal sheath abuts the proximal ring member and the distal end of the proximal sheath abuts the mid-ring member;

wherein further actuation of the distal and proximal sets of fingers are prevented by the abutment of the distal ring member by the distal sheath and the abutment of the proximal ring member by the proximal sheath, thereby providing tactile feedback to a user that the ring deployment mechanism has reached complete actuation.

17. The instrument of claim 16, wherein the actuation mechanism comprises a knob.

* * * * *